United States Patent [19]

Hobbs et al.

[11] 4,100,196

[45] Jul. 11, 1978

[54] PRODUCTION OF N-(ALKADIENYL)AMINES

[75] Inventors: Charles F. Hobbs, Des Peres; Dudley E. McMackins, St. Charles, both of Mo.

[73] Assignee: Monsanto Company, St. Louis, Mo.

[21] Appl. No.: 753,970

[22] Filed: Dec. 23, 1976

Related U.S. Application Data

[63] Continuation-in-part of Ser. No. 697,900, Jun. 21, 1976.

[51] Int. Cl.² ............................................. C07C 85/18
[52] U.S. Cl. ........................... 260/585 D; 252/431 C; 252/431 N; 252/431 P; 260/293.51; 260/326.8; 260/563 R; 260/563 C; 260/576; 260/577; 260/583 H; 260/584 R; 544/178; 544/404
[58] Field of Search ............... 260/247, 585 D, 563 R, 260/576, 563 C, 577, 584 R, 583 H; 252/431 C, 431 N, 431 P

[56] References Cited

PUBLICATIONS

Allum et al., "J. Organomet. Chem." vol. 87(2), pp. 189–201 (1975).
Baker et al., "J. Chem. Soc., Perkin Trans 2", pp. 1511–1517 (1974).

Primary Examiner—Daniel E. Wyman
Assistant Examiner—John J. Doll
Attorney, Agent, or Firm—Scott J. Meyer; John D. Upham

[57] ABSTRACT

In the process of producing N-(alkadienyl)amines by the amination of conjugated dienes in a hydroxylic solvent medium in the presence of a catalyst comprising a palladium compound co-catalyzed with a phosphonite ligand, the improvement in which the phosphonite ligand is polymerized with polyvinyl alcohol whereby the catalyst can be readily separated from the liquid rection products.

13 Claims, No Drawings

PRODUCTION OF N-(ALKADIENYL)AMINES

RELATED APPLICATIONS

This is a continuation-in-part of copending application Ser. No. 697,900, filed Jun. 21, 1976.

BACKGROUND OF THE INVENTION

This invention relates to the palladium-catalyzed amination of conjugated dienes to produce long-chain unsaturated amines. More particularly, this invention relates to an improved method of separating the soluble homogeneous catalyst from the liquid products of the palladium-catalyzed amination reaction.

The use of homogeneous catalysts for various organic syntheses is well-known. For useful background information in this field, reference can be had to the following comprehensive publications:

C. W. Bird, "Transition Metal Intermediates in Organic Synthesis," Academic Press, New York, N.Y., 1967.

"Homogeneous Catalysis," Adv. in Chem. Series 70, Amer. Chem. Soc., Washington, D.C., 1968.

J. Tsuji, "Organic Synthesis by Means of Transition Metal Complexes," Springer-Verlag, New York, N.Y., 1975.

P. M. Maitlis, "The Organic Chemistry of Palladium, Vol. II," Academic Press, New York, N.Y., 1971.

In many instances, homogeneous catalysts perform syntheses which are impossible to effect with heterogeneous catalysts or outperform their heterogeneous counterparts in rate or selectivity. Despite their great usefulness, many homogeneous catalysts have a drawback in that they are difficult to separate from the products of the catalysis. An ideal situation would be a "heterogeneous-homogeneous" catalyst which somehow would retain the chemical advantages of the soluble homogeneous catalysts but which could also be easily separated from the liquid reaction products.

Recently, in said copending application Ser. No. 697,900, filed June 21, 1976; the present inventors disclosed an improved homogeneous catalyst system which gives high yields of N-(alkadienyl)amines by reaction of conjugated dienes with primary and secondary amines as well as with ammonia. Notwithstanding the decided advantages of this catalyst system, difficulty is encountered in many instances in separating the liquid product from the soluble catalyst. Therefore, it was desired to develop means for improving the separation procedure.

BRIEF SUMMARY OF THE INVENTION

In accordance with the present invention, an improved method is provided for separating the soluble homogeneous catalyst from the liquid reaction products of the palladium catalyzed amination of conjugated dienes for the production of long-chain unsaturated amines. This palladium-catalyzed reaction is of the type described in said copending application, Ser. No. 697,900, filed June 21, 1976, said copending application being incorporated herein by reference. In said copending application, the conjugated dienes are reacted with ammonia and amines in a hydroxylic solvent medium and the catalyst system comprises a palladium compound co-catalyzed with a phosphonite ligand. By the improvement of the present invention, the catalyst is insolubilized by incorporating the phosphonite ligand as a polymeric phosphonite of polyvinyl alcohol. It has unexpectedly and surprisingly been found that the insolubilized catalyst not only retains essentially all of the good rate and selectivity characteristics of the soluble catalyst system but also can be more easily separated from the liquid reaction products, such as by filtration, and then reused several times with little or no loss of catalytic activity.

DETAILED DESCRIPTION OF THE INVENTION

The synthesis of the polymeric phosphonite ligand employed in this invention can be readily carried out by transesterification of the phosphonite with polyvinyl alcohol. This reaction is conveniently conducted in the presence of inert solvents at elevated temperatures and distilling off the liberated alcohol from the resulting insolubilized ligand product. Although a wide range of temperature conditions can be used, the temperature of the reaction generally ranges from about 100° to about 225° C, and preferably the temperature is about 150° C. In general, any solvent which is inert to the desired reaction product can be used as a reaction medium, for example, glycols and ethers such as diethylene glycol ethyl ether, diethylene glycol dimethyl ether, and the like solvents as well as hydrocarbons or chlorinated hydrocarbons such as xylene, dichlorobenzene and similar such solvents.

It should be realized that the invention is not limited to the above method of synthesizing the polymeric phosphonite ligand as other methods will be apparent to those skilled in the art.

The preferred phosphonites for use in making the polymeric phosphonite ligands are the dialkyl arylphosphonites having from about one to about four carbon atoms in the alkyl group such as the dimethyl, diethyl, dipropyl, diisopropyl and dibutyl arylphosphonites. The preferred aryl group in these phosphonites is phenyl. Other phosphonites having larger alkyl groups also can be used in this invention but are less advantageous inasmuch as the liberated alcohol has a higher boiling point and is therefore more difficult to remove.

The polyvinyl alcohol polymers used in making the polymeric phosphonite ligands include pure polyvinyl alcohols as well as the products of partial alcoholysis or hydrolysis which contain a sufficient number of free hydroxyl groups to render the material soluble in water. These polymers generally are prepared from polyvinyl acetate by replacement of the acetate groups with hydroxyl groups. The polyvinyl alcohols are well-known polymeric materials, having been described in early U.S. Pat. Nos. 1,672,156; 1,971,951; 2,109,883; and 2,513,488. Further background information on the polyvinyl alcohols can be had by reference to the monograph by Schildknecht, "Vinyl and Related Polymers," John Wiley & Sons, Inc. 1952, pp. 341-57. Polyvinyl alcohols are available commercially as high, medium or low viscosity types such as, for example, those available under the trademark Elvanol ® from duPont and under the trademark Gelvatol ® from Monsanto. These commercially available products generally have a molecular weight within the range of from about 14,000 to about 125,000.

The exact structure of the polymeric phosphonite ligand is not known but following general structure in which $m >> n$ is believed to be a reasonable one based on elemental analysis and the fundamental nature of the reactants using diethylphenylphosphonite as an example:

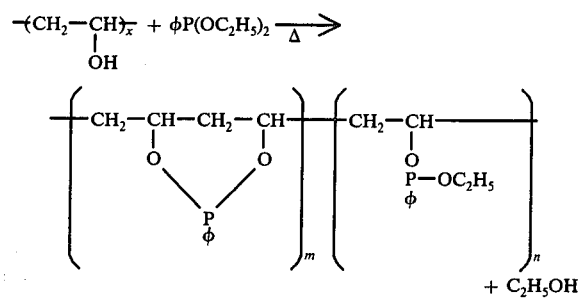

wherein $\phi$ = phenyl, and $x$ = about 300 to 3000.

This polymeric phosphonite ligand is a water-insoluble, granular material containing up to about 12% phosphorus. The phosphorus is attached to the polymer backbone through two oxygens in one of the repeating units ($m$) and through one oxygen in the other repeating unit ($n$).

The insolubilized catalyst used in this invention is formed in situ by contacting the polymeric phosphonite ligand with a palladium compound in alcoholic solution. The preferred palladium compounds are salts with readily displaceable anions such as, for example, acetate, nitrate and trifluoroacetate. The acetoacetate is substantially less effective, and salts with strongly bound anions such as halides are ineffective in this catalyst system.

Other suitable palladium compounds are the sulfonic acid esters such as, for example, tetrakis-(benzonitrile)-palladium(II)trifluoromethanesulfonate and palladium-(II)tetrakis(acetonitrile)trifluoromethanesulfonate.

The amount of the polymeric phosphonite ligand used in the insolubilized catalyst can vary somewhat. Generally an amount of polymeric phosphonite ligand such that the ratio of phosphorus to palladium is from one to about 15 parts of phosphorus to one part of palladium is suitable. The preferred ratio of phosphorus to palladium is about 6:1.

Examples of conjugated dienes which can be appropriately aminated with ammonia by the aforesaid catalyst system used in this invention are dienes having from four to about six carbon atoms such as, for example, butadiene, isoprene, 1,3-pentadiene, 2,4-hexadiene and 2,3-dimethylbutadiene. Certain larger molecules having a conjugated diene function such as 1,3,7-octatriene also can be aminated in accordance with this invention. Amination with butadiene is preferred.

In addition to the direct amination with ammonia with the catalyst system of this invention, amines can also be used in the amination reaction. Examples of suitable amines are monoalkylamines having from one to about 20 carbon atoms such as methylamine, ethylamine, propylamine, isopropylamine, butylamine, hexylamine, octylamine, octadecylamine, cyclohexylamine, cyclopentylamine, adamantylamine and ethanolamine; dialkylamines having from one to about 20 carbon atoms such as dimethylamine, diethylamine, dipropylamine, dibutylamine, dihexylamine, dioctylamine, dicyclohexylamine, N-methylcyclohexylamine and diethanolamine; alkenylamines such as allylamine, 2-butenylamine and 3-butenylamine; dialkenylamines such as diallylamine, dibutenylamine, 2,7-octadienylamine and bis-2,7-octadienylamine; heterocyclic amines, such as pyrrolidine, piperidine, morpholine and piperazine; aromatic amines having from one to about 20 carbon atoms such as aniline, methylaniline, phenylenediamines and N-phenylphenylenediamines; and alkylenediamines having from one to about 20 carbon atoms such as ethylenediamine, trimethylenediamine, tetramethylenediamine, pentamethylenediamine, hexamethylenediamine and octamethylenediamine.

The proportions of conjugated diene and ammonia or amine used in the palladium-catalyzed reaction of this invention can vary widely. Thus, at butadiene/ammonia mole ratios of 0.5 or higher, the predominant product is tris(2,7-octadienyl)amine. At lower ratios of butadiene/ammonia, a shift to the bis(2,7-octadienyl)amine is obtained. With regard to rate of reaction, best results are obtained with a butadiene/ammonia ratio of from about 3/1 to about 6/1.

The proportions of ammonia or amine and the palladium compound also can very widely and will depend in part upon the time and temperature of reaction. The preferred ratio of ammonia/palladium compound is from about 50/1 to about 250/1. In the case of the amines, the ratio of amine/palladium compound can range up to about 1000/1.

Use of a hydroxylic solvent for the reaction medium facilitates the rapid reaction rate of the amination. Solvents such as, for example, methanol, ethanol, propanol and phenol are preferred. Other suitable solvents are, for example, the glycols such as ethylene glycol, diethylene glycol and propylene glycol, and various other hydroxylic solvents such as butanol and 2,2,2-trifluoroethanol. Non-hydroxylic solvents such as acetonitrile, tetrahydrofuran, chlorobenzene, nitrobenzene, ethyl acetate, and diethyl ether are ineffective in the catalyst system of this invention.

Although reaction temperatures for the catalyst system defined herein can range from about 0° to about 150° C, temperatures of from about 50° to about 100° C are preferred in the case of using ammonia while temperatures of from about 25° to about 60° C are preferred when using amines. At temperatures substantially higher than 150° C, the dimerization of the butadiene becomes increasingly competitive while at temperatures substantially lower than 0° C the reaction proceeds undesirably slowly.

The following detailed examples will further illustrate the invention although it will be appreciated that the invention is not limited to these specific examples or the specific details disclosed therein.

EXAMPLE 1

Preparation of polymeric phosphonite ligand

A mixture of 8.8 grams (0.2 mole equivalent) of dried polyvinyl alcohol (available under the trademark Gelvatol ® 1-90 from Monsanto Company), 19.8 g (0.10 mole) of diethylphenylphosphonite and 25 ml of dried diglyme (dimethyl ether of diethylene glycol) were placed in a 100 ml distilling flask and heated under nitrogen at 150° C for several hours, during which time the solid polymer swelled and ethanol was slowly distilled off. A total of 6.3 grams of ethanol was collected. The rubbery product was triturated with several batches of diethyl ether and dried by filtration, all in a nitrogen atmosphere. Analysis of the product gave 12.28% phosphorous. This material was subsequently used for amination of butadiene in further examples (Example 2) below.

In a larger preparation of the polymeric phosphonite ligand, 48.4 g (1.1 mole equivalent) of the same polyvinyl alcohol, 108.5 g (0.55 mole) of diethylphenylphosphonite and 250 ml of diglyme were heated at 150° under nitrogen with stirring and removal of ethanol as before. When stirring became difficult, additional diglyme was added (in two portions of 150 ml and 100 ml). Reaction time was 8.5 hours, during which time 63 ml of ethanol was collected. The granular, off-white product was collected by filtration and washed with ether and dried, all under nitrogen; weight of product was 115.3 g; Elem. anal. C, 58.39%; H, 6.51%; P, 12.56%.

EXAMPLE 2

Amination with various amines and ammonia

In a 45 ml stainless steel bomb equipped with a pressure gauge, various amines or ammonia (80 mmoles) and butadiene (160 mmoles with sec. amines, 320 mmoles with primary amines and 480 mmoles with ammonia) were stirred with 0.25 g (1.11 mmoles) of palladium acetate, 5 ml of methanol and 1.56 g of polymerized phosphonite ligand (containing 12.28% phosphorus as in Example 1) at room temperature (about 20°–25° C).

This is equivalent to six moles of equivalent phosphorus per mole of palladium compound. In cases where no exotherm was noted within 30 minutes, the bomb was warmed to 60° C. The reaction was allowed to proceed until the internal pressure of the bomb reached near zero. The liquid products were filtered from the polymeric solid and identified as octadienylated amines by vapor phase chromatography.

In cases where the catalyst was recycled, the solid product filtered from the reaction mixture was washed with methanol and returned to the bomb. A new charge of amine or ammonia, butadiene and methanol was added and the reaction was rerun with only the used polymeric solid as the catalyst.

The foregoing amination reactions were carried out with morpholine, diethanolamine and ethanolamine as the exemplary amines and with ammonia to give mainly N-octa-2,7-dienylated products. Reaction rates and conversions to the octadienylated amines were comparable to those obtained using the free (unpolymerized) ligand. The results using the foregoing polymerized phosphonite ligand, along with the comparative results on the reactions using the free ligand, are set forth in the following tables I to IV:

| I. Amination With Morpholine at Room Temp. (25° C) | | | | |
|---|---|---|---|---|
| Ligand | Number of Times Catalyst Used | Reaction Time (min.) | Conversion % Amine VPC | ppm Pd in Amine Product |
| Free | 1 | 60 | 100 | ~4000 |
| Polymer | 1 | 60 | 100 | 600 |
| Polymer | 2 | 30 | 100 | 200 |

| II. Amination With Diethanolamine* | | | | |
|---|---|---|---|---|
| Ligand | Number of Times Catalyst Used | Reaction Time (min.) | Conversion % Amine VPC | ppm Pd in Amine Product |
| Free | 1 | 30 | 100 | ~4000 |
| Polymer | 1 | 45 | 95 | 3000 |
| Polymer | 2 | 45 | 98 | 200 |
| Polymer | 3 | 60 | 95 | 150 |

*At 60° C except with free ligand at room temp. (25° C)

| III. Amination With Ethanolamine at 60° C | | | | |
|---|---|---|---|---|
| Ligand | Number of Times Catalyst Used | Reaction Time (min.) | Conversion % Amine VPC | ppm Pd in Amine Product |
| Free | 1 | 180 | 100 | ~4000 |
| Polymer | 1 | 225 | 100 | 2000 |
| Polymer | 2 | 225 | 100 | 300 |

| IV. Amination With Ammonia* | | | | |
|---|---|---|---|---|
| Ligand | Number of Times Catalyst Used | Reaction Time (min.) | Conversion % Amine VPC | ppm Pd in Amine Product |
| Free | 1 | 60 | 95 | ~4000 |
| Polymer | 1 | 345 | 15 | ** |
| Polymer | 2 | 240 | 36 | 1533 |
| Polymer | 3 | 300 | 74 | 400 |
| Polymer | 4 | 300 | 76 | 300 |

*At 60° C with free ligand and 1st run with polymer; 100° C in 2d to 4th runs with polymer.
**Not determined.

Various other examples will be apparent to the person skilled in the art after reading the foregoing specification without departing from the spirit and scope of the invention and it is intended that all such examples be included within the scope of the appended claims.

What is claimed is:

1. The process of producing N-(alkadienyl)amines by reaction of conjugated dienes and ammonia or amines having from one to about 20 carbon atoms in a hydroxylic solvent medium in the presence of a catalyst comprising a palladium compound co-catalyzed with a polymeric phosphonite ligand, said phosphonite ligand comprising a phosphonite polymerized with polyvinyl alcohol.
2. The process of claim 1 in which the conjugated diene has from 4 to about 6 carbon atoms.
3. The process of claim 1 in which the conjugated diene is butadiene.
4. The process of claim 1 in which the conjugated diene is reacted with ammonia.
5. The process of claim 1 in which butadiene is reacted with ammonia.
6. The process of claim 1 in which the hydroxylic solvent is methanol.
7. The process of claim 1 in which the palladium compound is a salt of palladium and a readily replaceable anion.
8. The process of claim 1 in which the palladium compound is palladium acetate.
9. The process of claim 1 in which the phosphonite ligand is a polymer of polyvinyl alcohol and a dialkyl arylphosphonite having from about one to about four carbon atoms in the alkyl group.
10. The process of claim 9 in which the dialkyl arylphosphonite is diethylphenylphosphonite.
11. The process of claim 1 in which the conjugated diene is reacted with amine selected from the group consisting of morpholine, diethanolamine and ethanolamine.
12. The process of claim 1 in which butadiene is reacted with amine selected from the group consisting of morpholine, diethanolamine and ethanolamine.
13. The process of claim 1 in which butadiene is reacted with ammonia or an amine selected from the group consisting of morpholine, diethanolamine and ethanolamine, and in which the phosphonite ligand is a polymer of polyvinyl alcohol and diethylphenylphosphonite, the palladium compound is palladium acetate and the hydroxylic solvent is methanol.

* * * * *